United States Patent [19]

Katsumi et al.

[11] Patent Number: 5,054,908

[45] Date of Patent: Oct. 8, 1991

[54] METHOD AND APPARATUS FOR EVALUATING HUMAN VISUAL FUNCTION

[75] Inventors: Osamu Katsumi, Winchester, Mass.; Yoshitaka Miyanaga, Kawasaki, Japan

[73] Assignee: Eye Research Institute of Retina Foundation, Boston, Mass.

[21] Appl. No.: 251,699

[22] Filed: Sep. 30, 1988

[30] Foreign Application Priority Data

Oct. 1, 1987 [JP] Japan .......................... 62-150812[U]

[51] Int. Cl.⁵ ............................................... A61B 3/02
[52] U.S. Cl. .................................. 351/239; 351/243; 351/246
[58] Field of Search .............. 351/239, 243, 240, 241, 351/242, 246

[56] References Cited

U.S. PATENT DOCUMENTS 4,365,873 12/1982 Ginsburg ............................. 351/239
4,615,594 10/1986 Task .................................... 351/239

OTHER PUBLICATIONS

*Teller, D. Y., Morse, R., Borton, R., and Regal, D.:* Visual Acuity for Vertical Diagonal Grating in Human Infants, Vision Res. 14: 1433–1439, 1974.
*Katsumi, O., Oguchi, Y., and Uemura, Y.:* Assessment of Visual Ability in Infantile Esotropia Using the Preferential Looking Method, Jpn. J. Opthalmol. 25: 457–463, 1981.
*Katsumi, O., Oshima, T., and Uemura, Y.:* Development of Visual Acuity in Infant and Young Children up to Three Years Evaluated with the Preferential Looking Method, Opthalmic Pediatr. Genet. 2: 139–147, 1983.
*Dobson, V., Teller, D. Y., Lee, C. P., Wade, B.:* A Behavioral Method for Efficient Screening of Visual Acuity in Young Infants, I. Preliminary Laboratory Development, Invest. Ophthalmol. Vis. SCI. 17:1142–1150, 1978.

Primary Examiner—Rodney B. Bovernick
Attorney, Agent, or Firm—Lahive & Cockfield

[57] ABSTRACT

A method and apparatus for evaluating a human visual function employ a set of test objects that have viewing surfaces. One viewing surface bears no visually perceptible pattern and hence is visually homogeneous. Other viewing surfaces bear patterns of selected different coarseness corresponding to different visual acuities. The viewing surfaces preferably are otherwise visually identical and have selected luminosities. An examiner can readily evaluate a visual acuity function of a wide range of subjects, including infants, by observing the subject's eye motion to determine whether the subject distinguishes a perceptible pattern from the homogeneous pattern.

3 Claims, 3 Drawing Sheets

METHOD AND APPARATUS FOR EVALUATING HUMAN VISUAL FUNCTION

BACKGROUND OF THE INVENTION

This invention relates to a method and apparatus for evaluating a human visual function. More particularly, it pertains to measuring visual acuity, and in a manner particularly advantageous for use with a range of subjects, including infants and young children.

A determination of impaired or other below normal visual acuity is particularly desirable with infants and young children. Early detection can lead to remedial procedures that are often highly effective when begun at an early age. A measurement of visual acuity can provide diagnosis of a condition known as amblyopia, and more commonly termed lazy eye. As indicated, the correction of lazy eye is more successful when commenced at an early age, i.e. during infancy or early childhood.

Prior techniques for measuring visual acuity and hence an amblyopic condition are described in numerous publications, including:

Teller, D. Y., Morse, R., and Regal, D.: Visual Acuity for vertical and diagonal gratings in human infants. Vision Res. 14: 1433–1439, 1974;

Katsumi, O., Oguchi, Y., and Uemura, Y.: Assessment of visual ability in infantile esotropia using the preferential looking method. Jpn. J. Ophthalmol. 25: 457–463, 1981; and Katsumi, O., Oshima, T., and Uemura, Y.: Development of visual acuity in infant and young children up to three years evaluated with the Preferential Looking method. Ophthalmic Pediatr. Genet. 2: 139–147, 1983.

The evaluation of an amblyopic condition is difficult with subjects who can not speak or indicate a choice, and with those who are not readily tested with complex equipment. It hence is particularly difficult with infants and with young children.

For children over three years of age, it is known that one can evaluate visual function subjectively using the Landoldt letters. However, it is generally not possible to perform such a subjective test, as with the Landoldt letters, with subjects younger than three years of age or the like.

The technique which the present invention employs can, however, be used with such young children, as well as with infants and other humans with verbal communication limitation, including the mentally retarded and the brain damaged.

It is an object of this invention to provide an improved method and apparatus for evaluating a visual acuity function.

It is a further object to provide such a method and apparatus well suited for use with infants and young children and with other humans lacking in verbal communication.

Other objects of the invention are to provide a method and apparatus for measuring a human visual acuity function and further characterized by reliable measurement, low cost, and ease of use.

Other objects of the invention will in part be obvious and will in part appear hereinafter.

SUMMARY OF THE INVENTION

The apparatus and method of this invention evaluate human vision using a so-called preferential looking technique.

The preferential looking method which the invention employs is based upon the finding that infants, children and others typically prefer a patterned display, when presented with both a non-patterned display and a patterned display. It is established that commonly a subject able to perceive the pattern on the one display will discriminate between the two displays, and its eyes will be directed to the patterned display. By presenting two displays to a subject, typically simultaneously, and one bearing a visually perceptible pattern and the other being free of such a pattern, an examiner observes the eyes of the subject to determine whether the subject discriminated between the two displays. By using patterned displays one at a time and of different pattern coarseness, typically with progressively narrower grating-like patterns, the examiner is able to determine when the subject is no longer able to discriminate between the unpatterned display and the finely patterned display. The coarseness of the smallest pattern which the subject can discern is a measure of the visual acuity of that person.

Preferential looking equipment for performing this evaluation has previously generally been large and complex, typically using two viewing screens or projectors and a control device. Also, the prior equipment for acuity measurement with preferential looking has required a trained examiner. Hence visual testing with the preferential looking technique has generally been available only on a limited and restricted basis.

This invention solves these problems and thereby provides apparatus and a procedure with which one can evaluate visual acuity easily, by a relatively unskilled examiner, and with simple, compact and relatively low-cost equipment.

According to the invention, a method and apparatus for evaluating a human visual acuity function employ a set of test objects which an examiner can present for observation by a subject. Each object in the set has a viewing surface with a visual pattern different from that of other objects in the set. The patterns on different objects in the set range from no visually perceptible pattern to a minimally perceptible pattern to increasingly perceptible patterns. The patterns hence vary in coarseness, or resolution, from one test object to another. The visual patterns on the different objects in the set thus correspond to different visual acuities. The viewing surfaces on the objects are otherwise preferably visually identical, having identical shape. Further, the viewing surfaces of the different objects in the set have selected luminance, and preferably have substantially matching luminosity or substantially the same luminosity.

Features of the invention also include providing the elements of each patterned viewing surface with similar colors, and with an intermediate difference in optical contrast. With further regard to color, the pattern elements, e.g. the stripes and the spacings of a grating pattern, preferably have similar neutral, i.e. near-gray, colors that further are preferably the same. In one preferred embodiment, the pattern elements are gray with a blue-purple tint. The intermediate optical contrast between the pattern elements which the invention provides is typically substantially in the range of 25% to 80%, and preferably between 30% and 75%. This measure can be determined with the equation: Percent Contrast $= (L-D)/(L+D)$; where L and D are like measures of the luminance respectively of the optically lightest and of the optically darkest elements of the viewing pattern. These color and contrast features of the invention are in distinction to prior practices, that commonly display patterns of differently colored elements and of high contrast, typically black and white patterns.

Further in accord with the invention, the viewing surface patterns on the test objects preferably consist of pattern elements having either of two different selected luminance values. Thus the surface patterns typically consist of alternate grating-like segments that have either of the two different luminance levels. The grating-like segments on any one viewing surface preferably have the same coarseness, e.g. the same width, and this width is different on different viewing surfaces to provide the selected different corresponding acuity measures. Thus, the test objects according to the invention preferably have viewing surfaces that are visually indistinguishable from one another except that the pattern of grating-like segments or other pattern elements of each viewing surface differ from those of other viewing surfaces according to a selected difference in visual acuity.

In one preferred embodiment, each viewing surface pattern consists of parallel lineal grating-like elements. In another, the pattern consists of alternate circular grating-like elements arranged with circular symmetry, much like a bull's eye target.

Further in accord with the invention, a surface of each test object other than the viewing surface, and typically an opposite back surface, bears indicia indicating the orientation with which the object is being held by the examiner, and thus the orientation with which the examiner is displaying the viewing surface pattern to a subject. A further indicia typically applied to this other surface indicates the acuity measure of the viewing surface Pattern on that test object.

According to one specific embodiment of the invention, the acuity testing apparatus consists of a set of flat plate-like discs. One disc has a homogeneous appearing viewing surface, and the viewing surface on each of several other discs has a grating different from that of other of the gratings. The viewing surface patterns on the discs, including the homogeneous one, preferably all have matching mean luminosity. The disc with a homogeneous surface and the discs with a visible pattern are configured to be similar and preferably identical in appearance other than as to the coarseness or resolution of the pattern grating, and the several different gratings correspond to different visual acuities. The selected grating patterns can be applied, for example, with a printing technique.

An examiner evaluates the vision of a child or other person using this set of discs by holding, in one practice, two discs together with the unpatterned homogeneous disc in front of a patterned disc. The examiner separates the two discs, one to the right and the other to the left, symmetrically. At this time the examiner determines the subject's response by observing the eye movement of the subject. The examiner can also observe the subject's pointing toward one of the separated discs and, where the subject is able to speak, verbally identifying which disc is preferred. As known from prior studies, a given subject is understood consistently to select either the unpatterned disc or a patterned disc, and by far most subjects are understood to discriminate and choose a patterned disc when compared with an unpatterned disc. The examiner repeats the test, commencing each time with a seemingly unpatterned homogeneous disc in front of a patterned disc, and using patterned discs with different pattern coarseness on different tests. By thus changing the patterned disc from time to time, and noting the results of each test, the examiner determines the finest or smallest pattern which the subject distinguishes, and thereby determines the level of the subject's visual acuity.

The method for evaluating human visual acuity function according to the invention thus includes the steps of displaying concurrently to a subject a pair of viewing surfaces, one of which is free of a visually perceptible pattern and the other of which bears a pattern having a resolution corresponding to a selected visual acuity. The method further includes moving the two viewing surfaces relative to one another, preferably at a substantially uniform fixed distance, in front of the viewer. The examiner repeats these concurrently displaying and moving steps with pairs of viewing surfaces; each pair includes the homogeneous surface and different pairs include different visually perceptible patterns corresponding to different visual acuities.

The evaluating method further includes displaying the homogeneous viewing surface alone, i.e. without a perceptibly patterned viewing surface, prior to displaying the aforesaid pair of two surfaces. The method further includes commencing the concurrent display of a pair of surfaces with the two surfaces closely proximal to one another, and then moving them apart.

Further in accord with the invention, the method is performed with viewing surfaces on manually manipulative test articles which are manually moved to provide the foregoing display and movement steps. Other features of the method of the invention include providing the several viewing patterns with colors and with optical contrast, as described above.

The invention accordingly comprises the several steps and the relation of one or more of such steps with respect to each of the others, and comprises the apparatus embodying features of construction, combinations of elements and arrangements of parts adapted to effect such steps, as further exemplified in the following detailed disclosure, and the scope of the invention is indicated in the claims.

BRIEF DESCRIPTIONS OF THE DRAWINGS

For a fuller understanding of the nature and objects of the invention, reference is to the following detailed description and the accompanying drawings, in which FIG. 1 is a front view of a disc-shaped test article according to the invention and having a homogeneous, i.e. visually unpatterned, viewing surface;

DESCRIPTION OF ILLUSTRATED EMBODIMENTS

Referring to FIGS. 1-7, the illustrated apparatus for evaluating vision provides a set of viewing surfaces arranged so that pairs of the viewing surfaces can be displayed concurrently to a test subject and, further, so that during this display different ones of the surfaces can be moved, relative to a seemingly unpatterned surface. The illustrated embodiment, to this end, employs a set of articles A, each preferably disc-like as illustrated and each having a viewing surface B. The several articles A in the test set preferably have substantially identical shape, to be substantially identical visually, at least when viewed at the viewing surface B, except for the pattern which a viewing surface bears.

In the illustrated preferred embodiment, the set of articles A has a disc A-1 having a homogeneous surface 10, i.e., a viewing surface which bears no visually perceptible pattern. The test set further has discs A-2, A-3, A-4, A-5 and A-6, each of which has a visually-different pattern of gratings 20, 21, 22, 23, and 24, respectively, on its viewing surface. The illustrated several gratings 20-24 differ in width as appears in FIGS. 2-7. The test set has a further disc A-7 structurally identical to the others and having the same grating pattern with even finer resolution, which is not shown.

Figure 3:
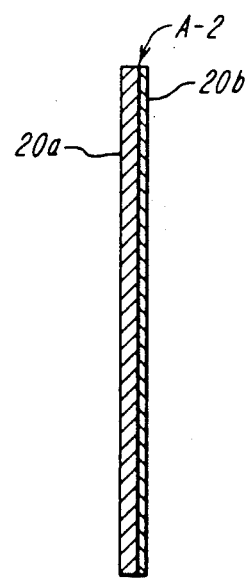
FIG. 3 is a side view of the disc-like article of FIG. 2.
Figure 4:
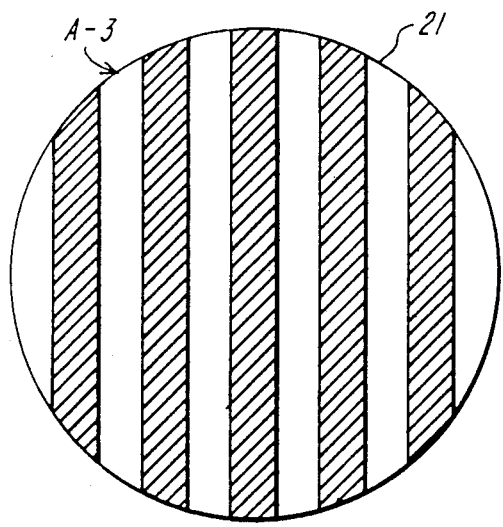
FIGS. 4, 5, 6 and 7 are each front views, similar to FIGS. 1 and 2, of further disc-like test articles according to the invention and each with a viewing surface patterned with progressively finer stripes or gratings, and accordingly corresponding to progressively different measures of visual acuity.
Figure 5:
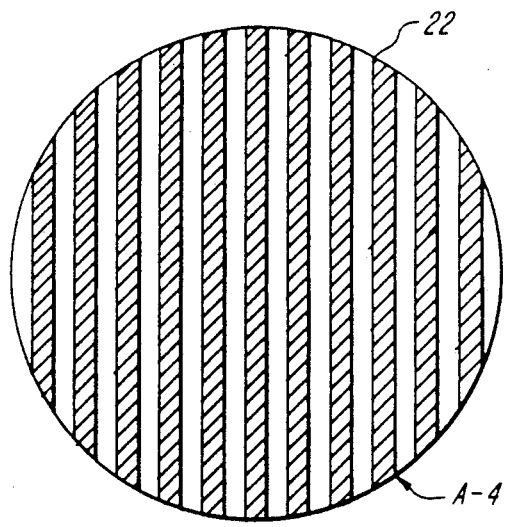
Figure 6:
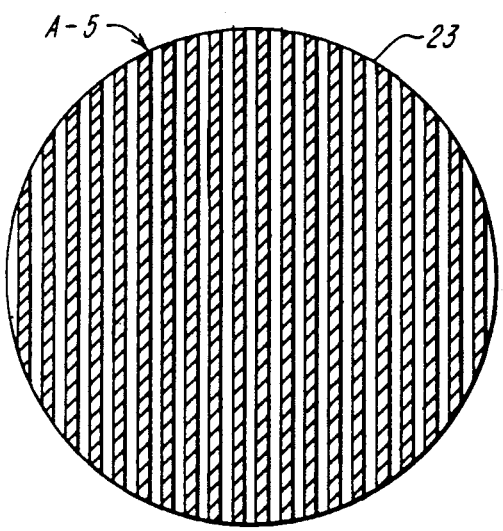
Figure 7:
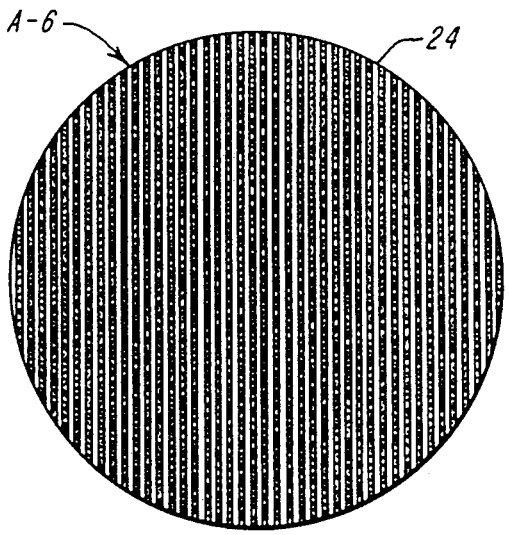

The discs A-1 ... A-7, as illustrated, are structurally identical flat circular plates, each with a flat planar viewing surface B, typically of nine cm diameter. As shown in FIG. 3, each test disc preferably is made with a circular plastic plate 20A which bears a selected viewing surface typically formed by affixing a viewing layer 20B that is either the homogeneous surface or a selected pattern. The test objects are designed and configured to be easily handled and stacked in register with one another.

The widths of the gratings 20-24 as illustrated are, by way of example, 16 mm, 8 mm, 4 mm, 2 mm and 1 mm, respectively. This grating dimension on disc A-7 is 0.50 mm. The stripes and the lineal spaces between the stripes on each disc have equal width, each equal to one of the foregoing dimensions. The corresponding visual acuity at a test distance of 50 cm is 0.01 (20/2200) with the 16 mm grating 20; 0.018 (20/1100) with the 8 mm grating 21; 0.036 (20/550) with the 4 mm grating 22; and 0.072 (20/275) with the 2 mm grating 23. The acuity is 0.14 (20/138) with the 1 mm grating 24 and is 0.29 (20/69) with the 0.5 mm grating of disc A-7.

Figure 1:
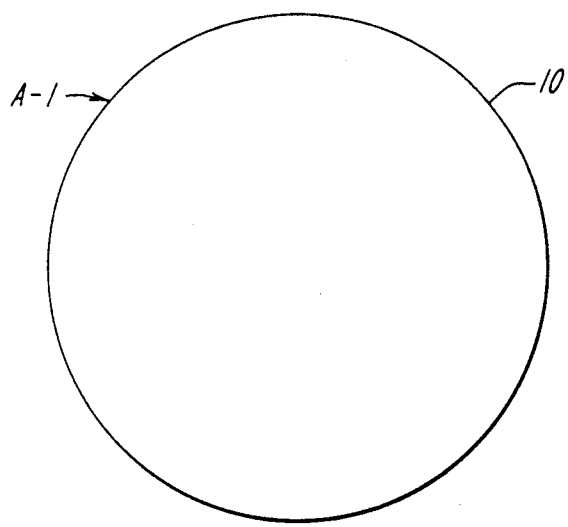
Figure 2:
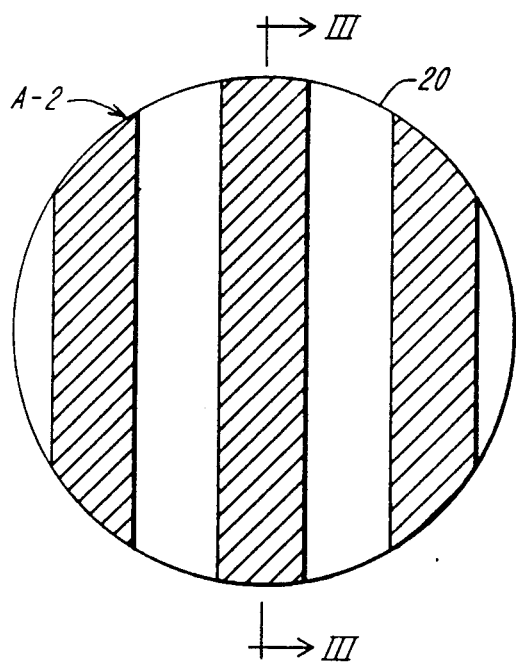
FIG. 2 is a view similar to FIG. 1 of another disc-like test article with a viewing surface patterned with stripes.

The disc A-1 of FIG. 1 with no visually perceptible pattern preferably in fact has a grating pattern corresponding to a visual acuity of 0.58 (20/34) formed by gratings similar to those shown in FIGS. 2-7 and with a grating width of 0.25 mm.

One preferred technique for generating these lineal parallel grating patterns is with a computer graphic display and by copying or photographing the resultant grating pattern produced on a cathode-ray tube monitor for the computer system. This technique has the advantage of producing each grating pattern with the prescribed width, i.e. coarseness. Other techniques can be used for generating the patterns as apparent to one skilled in the art.

When the test distance, which is the distance from the front of a subject's eyes to the plane in which two discs A are displayed, is increased to 55 cm, the visual acuities are easier to evaluate, and are as follows for the discs A-1 ... A-7 of the illustrated embodiment:

| Grating Space | Visual Activity |
| --- | --- |
| 16 cm | 20/1920 |
| 8 cm | 20/960 |
| 4 cm | 20/480 |
| 2 cm | 20/240 |
| 1 cm | 20/120 |
| 0.5 cm | 20/60 |
| 0.25 cm | 20/30 |

It further is preferred that the contrast of each grating pattern not be very high, preferably lower than 80% to be close to a natural environment. The color of the grating pattern can be achromatic, such as gray. It is deemed desirable however to simulate a natural visual condition and therefore to tint each viewing surface pattern to attain a grating having blue-purple stripes of less than 80% contrast and greater than 30% contrast, i.e. an intermediate contrast level, on a faint blue-purple background visible in the space between the grating stripes. Further, the test disc A-1 having no visually perceptible grating on the viewing surface is preferably prepared with a like blue-purple color. As noted, however, the homogeneous surface pattern for this disc preferably is prepared identically as the other discs with a grating pattern too fine to be perceived, for example, with a 0.25 mm grating as stated above.

In either case, the mean luminosity of the viewing surface on the so-called unpatterned disc A-1 is matched to that of the other discs A-2 ... A-7; a preferred mean luminosity level is 150 candles per square meter.

That is, the discs of the test set preferably are provided with viewing surfaces having equal overall luminance, as measured for example with a luminance meter. The mean luminosity level of both the disc A-1 and each other disc A-2 ... A-7 is matched or balanced in this manner so that an examiner can perform a visual acuity examination in accordance with the invention without the subject being influenced by a luminosity difference. Thus luminosity preferably is another parameter of the viewing surfaces that is made equal so that the only difference in appearance between the viewing surfaces of a set is the coarseness, or resolution, of the pattern which each bears. Moreover, the shape of each disc is not necessarily circular as illustrated but can have other configurations including such illustrative examples as an ellipse or a rectangular, to name only a few.

It further is preferred that the pattern on each test disc be formed with pattern elements having essentially the same color, i.e. reflecting the same optical wave length of illuminating light, and with elements having either of two different luminosities. A preferred illustrative practice employs a pattern in which the dark elements, e.g. stripes as shown in the embodiments of FIGS. 2 and 4-7, have one-half the luminance of the space between those dark stripes.

It will also be noted that the different patterns on the discs of the illustrated test set differ by an octave, i.e. the interval in spacing between patterns of successive coarseness is a factor of two in the illustrated embodiment. The invention can be practiced with test patterns differing by other factors. A test set having patterns with a greater difference provides a less precise determination of visual acuity, whereas a test set having a smaller interval between the coarseness of successive patterns provides an acuity measurement of higher precision.

An evaluation of human visual function using the set of disc-like test articles A as described above with reference to FIGS. 1–7 is performed as follows.

Assuming the subject is an infant, it is comfortably positioned, suitably on its mother's lap. The examiner sits in front of the subject at a distance appropriate to hold the test articles in front of the eyes of the subject by a distance of typically 50 or 55 cm, to attain the acuity measures listed above for the illustrated test articles of FIGS. 1–7. The examiner typically has a centimeter scale for verifying this distance, in order to enhance the accuracy of the determination. The examiner holds the homogeneously appearing disc A-1 in front of a visibly patterned disc, so that the homogeneous disc conceals the viewing surface of the other disc. The examiner then moves the discs apart, e.g. vertically or horizontally, to show both discs to the subject, and to move them relative to one another.

Figure 8:
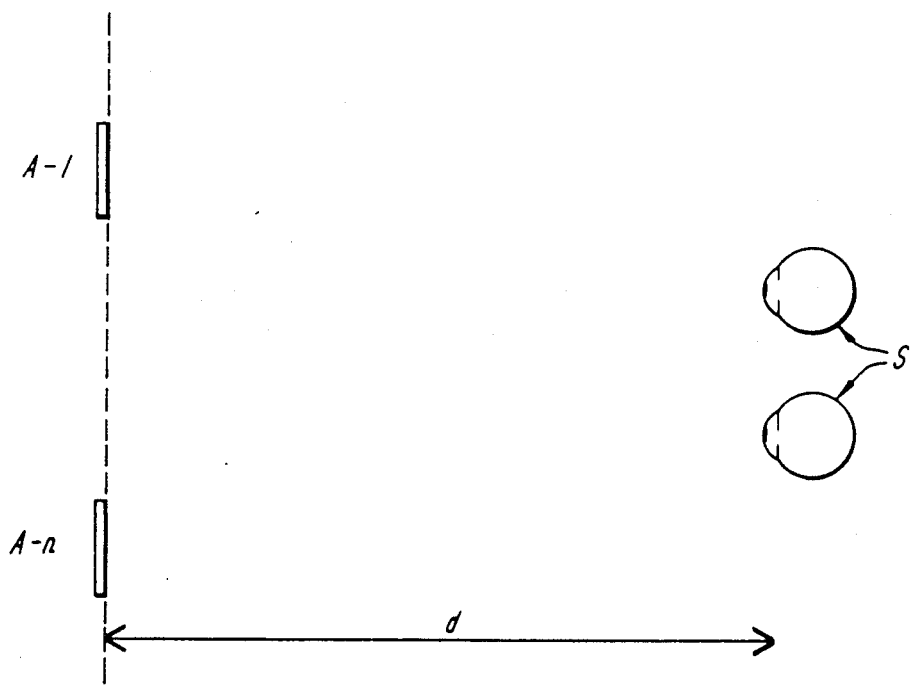
FIG. 8 is a plan view indicating the test procedure according to the invention.

The diagrammatic top view in FIG. 8 designates the subject's eyes S located at a viewing distance D from a vertical plane in which the examiner holds the two discs, one being the unpatterned disc A-1 and the other being a patterned disc A-2 or A-3 . . . A-7. The discs are held at essentially the same level as the viewer. As the examiner moves the discs from the initial position, where the unpatterned disc A-1 conceals the patterned disc, to the separated condition where both discs are displayed to the subject, the examiner views the eyes of the subject and determines whether the subject discriminates the pattern on one disk, i.e. perceives the stripes 21 or other pattern. The movement of the discs relative to one another facilitates the examiner in determining whether the subject discriminates the patterned viewing surface.

When the subject is an infant as young as around eighteen months of age, even though he or she normally can discriminate the patterns from the homogeneous viewing surface on the disc A-1, such a subject normally is not able to point to the patterned disc nor able to express a difference verbally. The examiner thus makes a judgment whether the subject discriminates between the two discs by watching the eye movement of the subject. When the subject is around two years of age, it typically can point to the patterned disc or verbally express a preference. It is generally preferred prior to examination for the examiner to allow the subject, particularly a child, to become familiar with the discs and even to have enhanced interest in the patterned disc by showing the discs and letting them be touched and otherwise examined. By doing so for a subject approximately two years or older, when it is able to discriminate the pattern, the examiner can ask the subject to explain a preference and as a result attain an easier and more reliable examination.

The examination is repeated, typically several times using the same patterned disc. When the percentile of correct responses is above 70%, and preferably above 75%, the examiner proceeds to the disc having the next higher resolution pattern, e.g. with narrow (higher frequency) stripes. For example, when the examiner changes from the FIG. 4 disc A-3 to the FIG. 5 disc A-4, the stripes then being used correspond to a visual acuity of 0.036, at a measuring distance of 50 cm.

On the other hand, when the examiner determines that the percent of correct responses is lower than in the order of 70%, the visual acuity of the subject corresponds to the pattern one octave or other increment in resolution higher than that of the disc then being used. It is to be understood that the testing distance can be changed, for example to one meter or 1.5 meter, depending on factors such as the age of the subject and the acuity level of the subject.

In this manner, by holding the homogeneous disc A-1 successively with different ones of the A-2 . . . A-7 with stripes, the examiner performs a preferred looking examination that quickly and effectively evaluates the visual acuity of a subject, even of a young child or an infant. The invention enables one to attain this result with minimal equipment and with relatively low skills for an ophthalmology clinic.

Indicia on the back surface of each disc identifies the visual acuity to which the pattern on that disc corresponds. Further indicia is preferably provided on the disc back surface for indicating the orientation of the pattern on the front viewing surface. This orientation indicia enables the examiner to display each patterned viewing surface with the same orientation, e.g. with pattern stripes consistently oriented vertically as appears in FIGS. 2-7.

It is also to be understood that one can manufacture test objects in accordance with the invention by directly applying an acuity pattern or visual homogeneous surface in a variety of ways on test objects of a variety of materials, including thick paper material or wood, among others.

Figure 9:
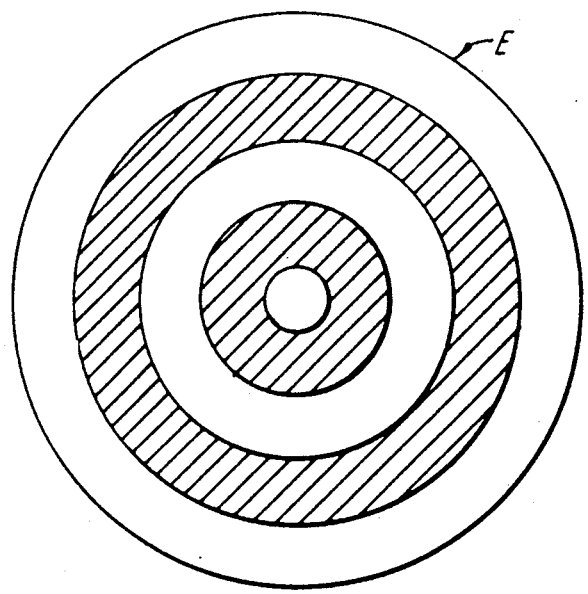
FIG. 9 is a view similar to FIGS. 1 and 2-7 showing another test article viewing surface according to the invention.

Moreover, FIG. 9 illustrates that a test article according to the invention can employ a pattern having circular geometry, rather than a lineal pattern as illustrated in FIGS. 2-7. FIG. 9 shows a single test object E having such a circular grating-like pattern. It will be understood that a set of such patterns is provided for practice of the invention, and the several test article have different circular patterns corresponding to different visual acuities.

It will thus be seen that the method and apparatus of the invention include the evaluation of a visual function with a test article having a visually homogeneous viewing surface and with a number of further test articles having patterned viewing surfaces of different visual resolution, and all with matching mean luminosity. The test article with the homogeneous viewing surface and those with visible patterns employ the same shape, to be identical in appearance to a subject. Each different pattern resolution corresponds selectively to a different visual acuity.

An examiner can easily perform a visual acuity measurement by holding the article with the visually homogeneous surface and a visually patterned article, and moving them relative to one another. Since large and complex apparatus is not required, one can provide equipment according to the invention at an ophthalmology clinic, and one can easily perform such a visual vision examination on a variety of human subjects, including infants and other young children.

It will thus be seen that the objects set forth above, among those apparent from the preceding description, are efficiently attained. Since certain changes may be made in carrying out the above method and in the articles set forth without departing from the scope of the invention, it is intended that all matter contained in the above description or shown in the accompanying drawings be interpreted as illustrative and not in a limiting sense.

It is also to be understood that the following claims are intended to cover all generic and specific features of the invention described herein, and all statements of the scope of the invention which, as a matter of language, might be said to fall therebetween.

Having described the invention, what is claimed as new and secured by Letters Patent is:

1. A method for evaluating a human visual acuity comprising the steps of
   A. displaying concurrently to a subject a pair of first and second viewing surfaces, a first of which is free of visually perceptible pattern and the other of which has a pattern corresponding to a selected visual acuity,
   B. moving said first and second viewing surfaces relative to one another at substantially uniform distance from the subject; and
   C. repeating said steps of concurrently displaying and relatively moving with pairs of viewing surfaces, each including said first viewing surface and successively including different visually perceptible patterns corresponding to different visual acuities.

2. A method according to claim 1 further characterized by the steps of
   A displaying said first viewing surface without said second viewing surface prior to said concurrently displaying step, and
   B. concurrently displaying said viewing surfaces with said second surface initially closely proximal to said first surface and initially moving said first and second viewing surfaces from said close proximity disposition to greater separation.

3. A method according to claim 1 further characterized by the step of
   A. providing said viewing surfaces on manually manipulative test articles and manually moving two said test articles, each of which bears at least one said viewing surface for performing said concurrently displaying and relatively moving steps.

* * * * *